(12) United States Patent
Barry et al.

(10) Patent No.: US 7,699,876 B2
(45) Date of Patent: Apr. 20, 2010

(54) MULTI-AXIAL BONE FIXATION APPARATUS

(75) Inventors: David Barry, Brooklyn, NY (US); Rui J. Ferreira, Livingston, NJ (US); Kirk J. Bailey, Blairstown, NJ (US)

(73) Assignee: EBI, LLC, Parsippany, NJ (US)

( * ) Notice: Subject to any disclaimer, the term of this patent is extended or adjusted under 35 U.S.C. 154(b) by 652 days.

(21) Appl. No.: 11/594,316

(22) Filed: Nov. 8, 2006

(65) Prior Publication Data

US 2008/0108992 A1 May 8, 2008

(51) Int. Cl.
*A61B 17/70* (2006.01)
(52) U.S. Cl. .................. 606/266; 606/267; 606/268; 606/269; 606/270; 606/272
(58) Field of Classification Search ............... 606/246, 606/264–279; 403/76–77; 411/377, 396, 411/517, 530
See application file for complete search history.

(56) References Cited

U.S. PATENT DOCUMENTS 4,946,458 A 8/1990 Harms et al.
(Continued)

FOREIGN PATENT DOCUMENTS

WO WO-0072770 12/2000
(Continued)

OTHER PUBLICATIONS

International Search Report and Written Opinion mailed Apr. 28, 2008 for PCT/US2007/023423.

*Primary Examiner*—Eduardo C Robert
*Assistant Examiner*—Steven J Cotroneo
(74) *Attorney, Agent, or Firm*—Harness, Dickey

(57) ABSTRACT

A bone fixation device. The bone fixation device includes a receiver having a deformable portion, a bone fastener having a head, the head insertable into the receiver from the deformable portion, and a retaining member couplable to the deformable portion. The retaining member deforms the deformable portion and angulatably retains the fastener relative to the receiver.

22 Claims, 6 Drawing Sheets

U.S. PATENT DOCUMENTS

| | | | |
|---|---|---|---|
| 5,549,608 A | 8/1996 | Errico et al. | |
| 5,728,098 A | 3/1998 | Sherman et al. | |
| 5,733,285 A | 3/1998 | Errico et al. | |
| 5,817,094 A | 10/1998 | Errico et al. | |
| 5,954,725 A | 9/1999 | Sherman et al. | |
| 6,010,503 A | 1/2000 | Richelsoph et al. | |
| 6,132,432 A | 10/2000 | Richelsoph | |
| 6,132,434 A | 10/2000 | Sherman et al. | |
| 6,254,602 B1 | 7/2001 | Justis | |
| 6,273,888 B1* | 8/2001 | Justis | 606/272 |
| 6,280,442 B1* | 8/2001 | Barker et al. | 606/60 |
| 6,287,311 B1 | 9/2001 | Sherman et al. | |
| 6,355,040 B1 | 3/2002 | Richelsoph et al. | |
| 6,371,957 B1 | 4/2002 | Amrein et al. | |
| 6,454,773 B1 | 9/2002 | Sherman et al. | |
| 7,022,122 B2 | 4/2006 | Amrein et al. | |
| 2001/0047173 A1* | 11/2001 | Schlapfer et al. | 606/72 |
| 2004/0176766 A1* | 9/2004 | Shluzas | 606/65 |
| 2005/0080415 A1* | 4/2005 | Keyer et al. | 606/61 |
| 2005/0096653 A1 | 5/2005 | Doubler et al. | |
| 2005/0228392 A1 | 10/2005 | Keyer et al. | |
| 2006/0129149 A1 | 6/2006 | Iott et al. | |
| 2007/0118117 A1 | 5/2007 | Altarac et al. | |

FOREIGN PATENT DOCUMENTS

| | | |
|---|---|---|
| WO | WO-2004089245 | 10/2004 |
| WO | WO-2005018471 | 3/2005 |
| WO | WO-2005041821 | 5/2005 |
| WO | WO-2005096968 | 10/2005 |
| WO | WO-2006047555 | 5/2006 |
| WO | WO-2006060585 | 6/2006 |

* cited by examiner

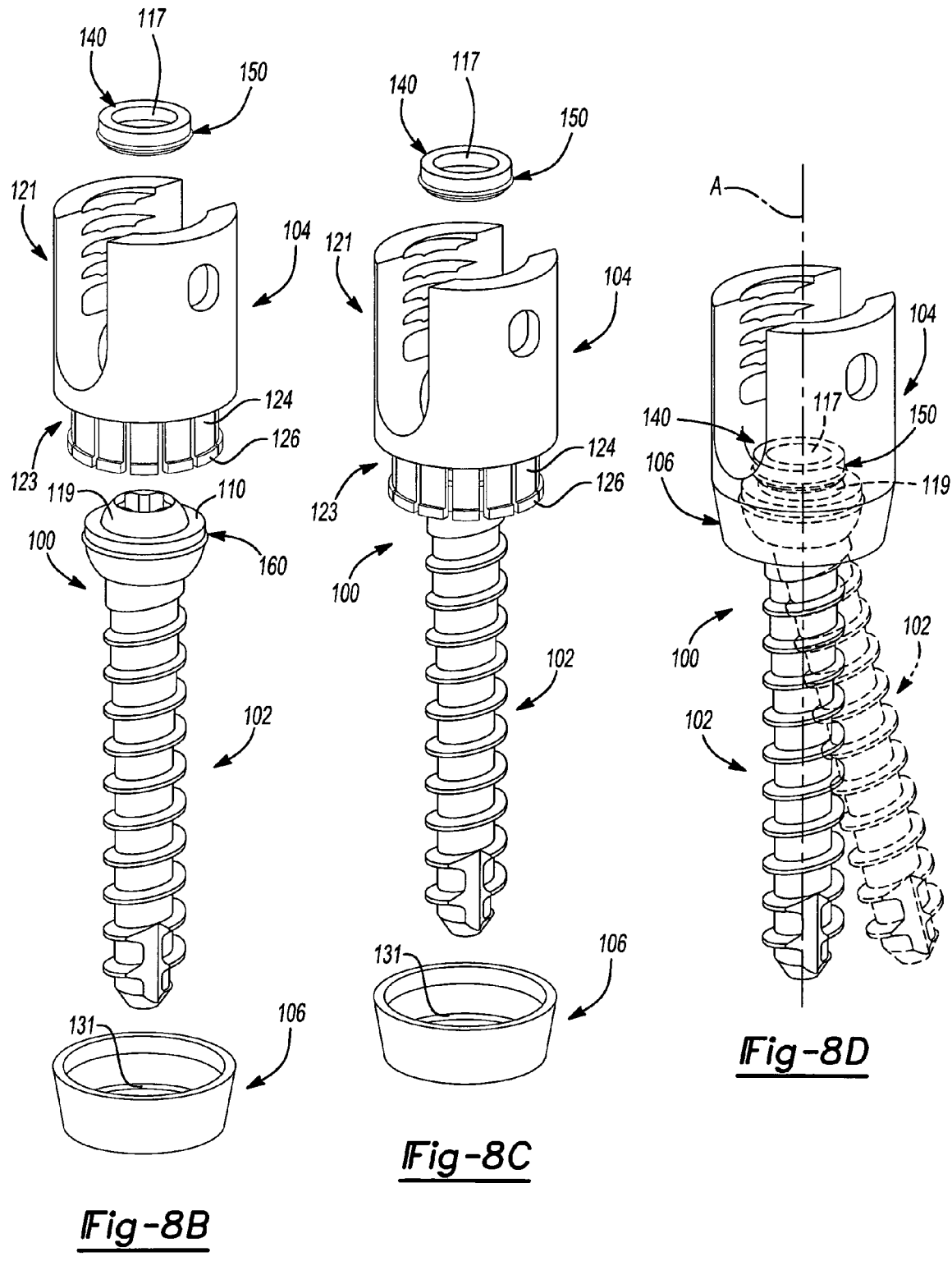

MULTI-AXIAL BONE FIXATION APPARATUS

It is often necessary to stabilize and fix bones in relation to one another to correct fractures, discontinuities or other abnormalities using fixation devices. Known devices for spinal fixation, for example, may include bone screws anchored in adjacent vertebrae and connected together by spinal rods. The spinal rods may be coupled transversely to the bone screws by saddle-like receiver components that also receive the bone screws. Multi-axial bone screws, when used, may pivot in corresponding sockets defined by the receivers. In some known devices, the bone screws can be introduced from the bottom rather than the top of the receivers.

It is still desirable to have multi-axial bone screw devices that can be easily assembled by the surgeon and secured at various orientations determined by the surgeon during implantation.

SUMMARY

The present teachings provide a multi-axial bone fixation device. The bone fixation device can include a receiver defining an axial opening along a longitudinal axis, the receiver having first and second portions along the longitudinal axis, the second portion being radially compressible, a bone fastener having a head, the head insertable into the axial opening in a direction from the second portion to the first portion, and a hollow member received around the second portion, the hollow member compressing the second portion and retaining the head while allowing angulation of the fastener relative to the longitudinal axis.

The present teachings also provide a multi-axial bone fixation device that includes a receiver defining an axial opening along a longitudinal axis, the receiver having an upper portion and a lower portion along the longitudinal axis, the lower portion comprising a plurality of spaced apart flexible elements, a bone fastener having a head and a bone-engaging elongated portion, the head insertable into the axial opening along the longitudinal axis in a direction from the lower portion to the upper portion, the head having an external circumferential groove, a friction element supported in the circumferential groove, and a hollow member having a surface tapered along the longitudinal axis and received around the lower portion, the hollow member compressing the plurality of flexible elements such that the fastener is retained in the receiver and permitted to angulate relative to the longitudinal axis.

The present teachings provide a multi-axial bone fixation device that can include a receiver defining an axial opening along a longitudinal axis, and a transverse opening along a transverse axis, the receiver having an upper portion and a lower portion along the longitudinal axis, the lower portion comprising a plurality of spaced apart elongated elements, each elongated element having a flange extending proximate a distal end thereof, and a bone fastener having a head and a bone-engaging elongated portion, the head insertable into the axial opening along the longitudinal axis in a direction from the lower portion to the upper portion, the head having a first circumferential groove. The fixation device can also include an annular member insertable into the axial opening from the upper portion over the head of the fastener, the annular member having a second circumferential groove, a first retention element supported in the first circumferential groove, a second retention element supported in the second circumferential groove, and a hollow member having a surface tapered along the longitudinal axis and received around the lower portion, the hollow member defining an inner groove engaging the flanges of the elongated elements and compressing the elongated elements such that the fastener is retained in the receiver and can angulate relative to the longitudinal axis. Further, the fixation device can include an elongated element insertable in the receiver along the transverse axis, and a securing element threadably received in the upper portion of the receiver over the elongated element, such that when the securing element is fully threaded to the receiver, the securing element transmits a force to the head of the fastener and secures the fastener in the receiver at a selected angle relative to the longitudinal axis.

The present teachings further provide a bone fixation device including a receiver having a deformable portion, a bone fastener having a head, the head insertable into the receiver from the deformable portion, and a retaining member couplable to the deformable portion. The retaining member deforms the deformable portion and angulatably retains the fastener relative to the receiver.

Further areas of applicability of the present invention will become apparent from the description provided hereinafter. It should be understood that the description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein:

FIGS. 8B-D illustrate various aspects of assembling the multi-axial screw assembly of FIG. 8A;

DESCRIPTION OF VARIOUS ASPECTS

The following description is merely exemplary in nature and is in no way intended to limit the invention, its application, or uses. For example, although the present teachings are illustrated with particular components used in spinal fixation, the present teachings can be used with other anchoring components and procedures.

Figure 1:
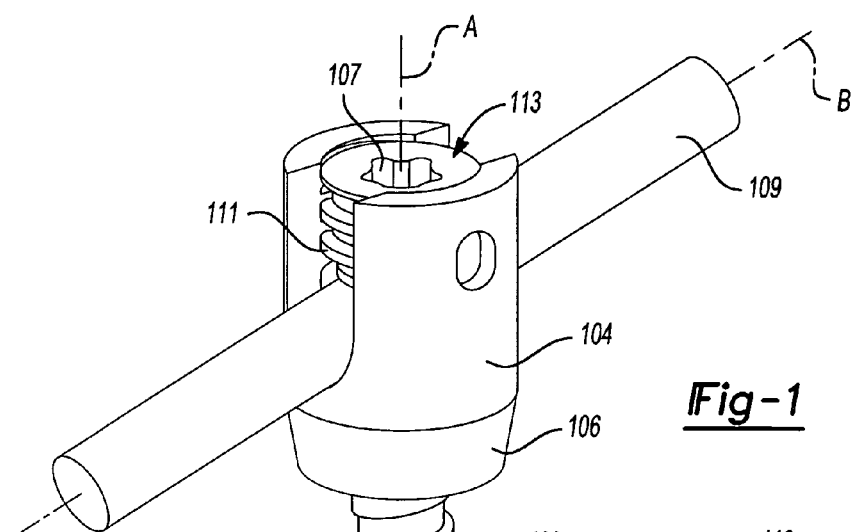
FIG. 1 is a perspective view of an exemplary multi-axial screw assembly according to the present teachings.

Referring to FIG. 1, an exemplary multi-axial bone fixation device 100 according to the present teachings is illustrated as assembled with a spinal connecting element 109. The connecting element 109 can be in the form of a rod or bar or other elongated element. Although the connecting element 109 is illustrated as straight, it will be appreciated that the connecting element 109 can be also curved and can have a curvature following, for example, the natural curvature of the spine.

Figure 2:
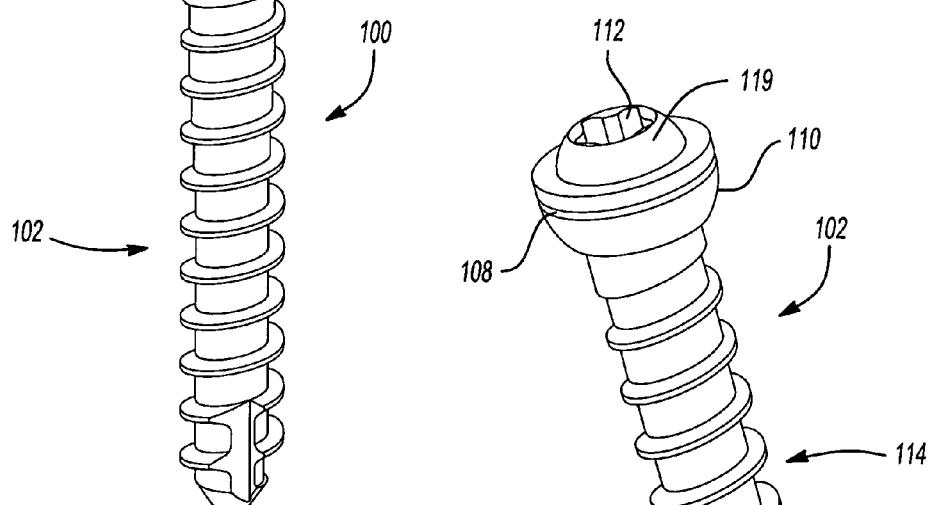
FIG. 2 is a perspective view of an exemplary bone screw of the multi-axial screw assembly of FIG. 1.
Figure 8A:
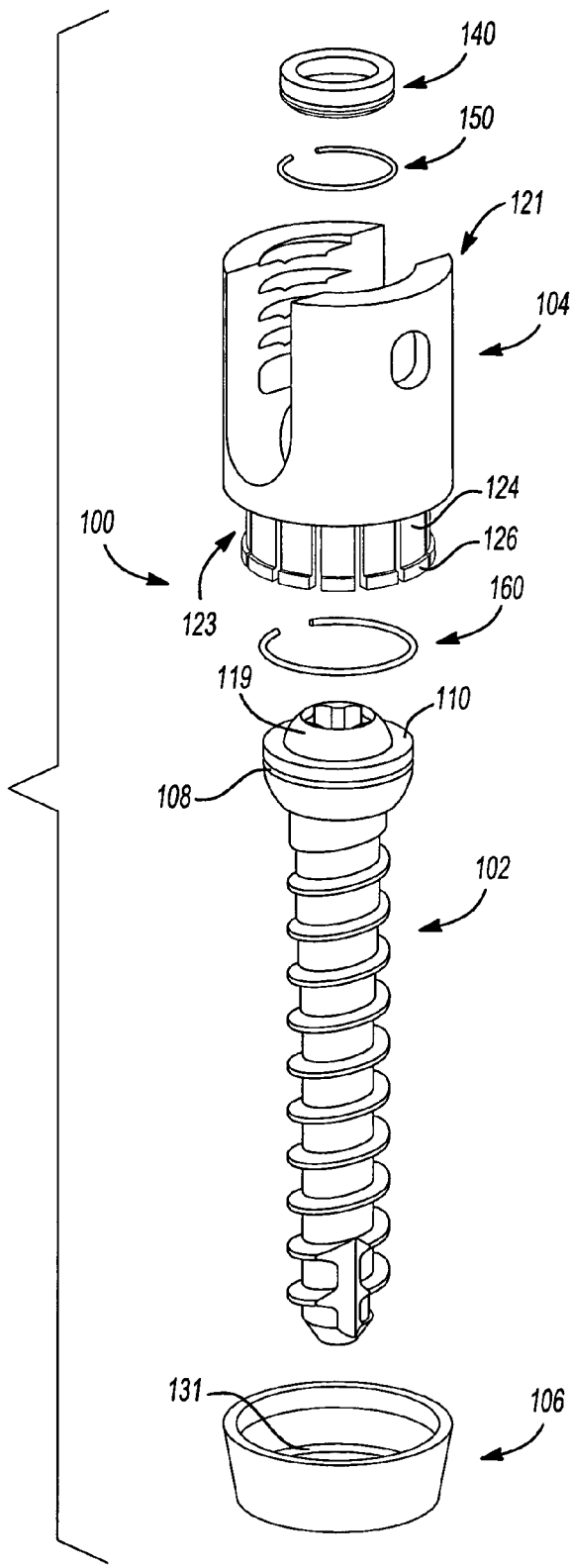
FIG. 8A is an exploded view of an exemplary multi-axial screw assembly according to the present teachings.

Referring to FIGS. 1, 2 and 8A, the bone fixation device 100 can generally include a bone fastener 102, a receiver 104, a hollow retaining member or sleeve 106, an annular element 140 and first and second retention elements 160, 150 shown in the form of split rings. Additional views of these components are illustrated in FIGS. 3A-7 and 9-10C.

Referring to FIG. 2, the bone fastener 102 can include a head 110 and a bone-engaging elongated portion 114 that can include ridges, threads or other anchoring formations 116 along at least a portion of its length. The elongated portion 114 can include one or more cutting flutes 118 at its distal end. The head 110 of the bone fastener 102 can define a first circumferential groove 108 for at least partially receiving the first retention element 160. The head 110 can include a protrusion 119 having an internal driver-engagement surface 112 for engaging a conventional or other insertion tool (not shown). The engagement surface 112 can include straight or curved drive faces. In the exemplary illustration of FIG. 2, a five-lobe (pentalobe) engagement surface 112 is shown for use with an insertion tool having complementary driver surfaces.

Figure 3A:
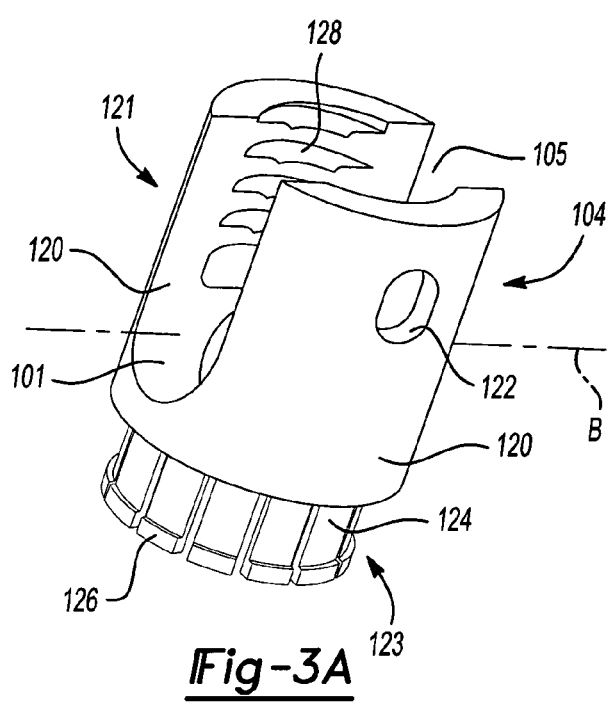
FIGS. 3A and 3B are perspective views of a receiver for the multi-axial screw assembly of FIG. 1.
Figure 3B:
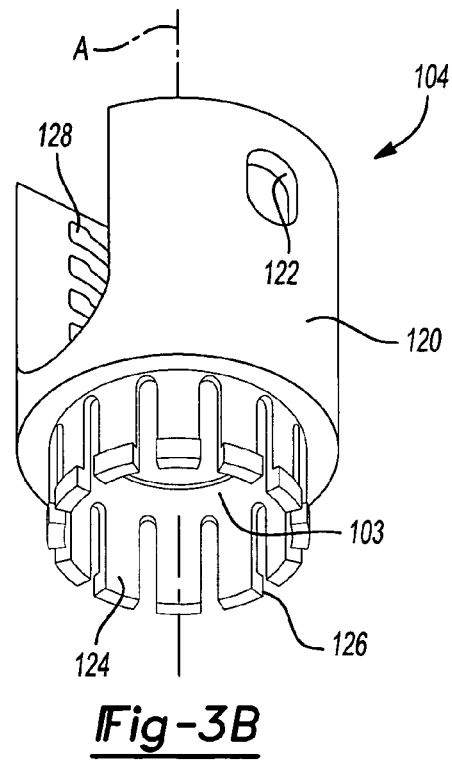

Referring to FIGS. 3A and 3B, the receiver 104 can define an axial opening comprising an upper opening 105 and a lower opening 103 along a longitudinal axis A. The receiver 104 can also include an upper portion 121 comprising two arms 120 and defining a U-shaped transverse opening 101 along a transverse axis B. Each of the arms 120 can define inner engagement formations 128, such as threads, ridges, or grooves. The transverse opening 101 can be configured to receive a connecting element, such as the connecting element 109 shown in FIG. 1. The receiver 104 can include a radially compressible lower portion 123 in the form of a socket defined by a plurality of spaced apart elongated elements or fingers 124. Each elongated element 124 can include an outward flange 126 directed radially away from the lower opening 103. The elongated elements 124 can be resiliently deflected inward toward the longitudinal axis A for receiving the hollow member 106.

Figure 4A:
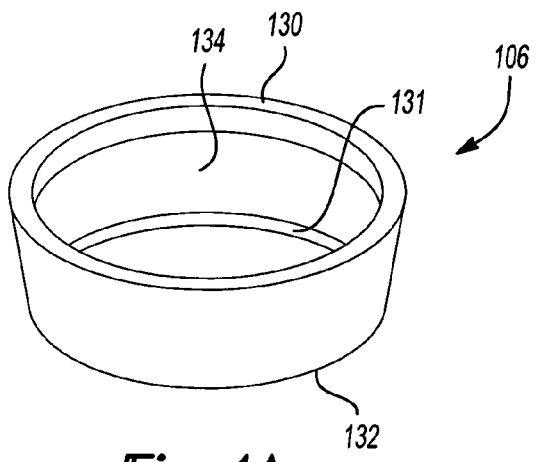
FIGS. 4A and 4B are perspective views of a sleeve for the multi-axial screw assembly of FIG. 1.
Figure 4B:
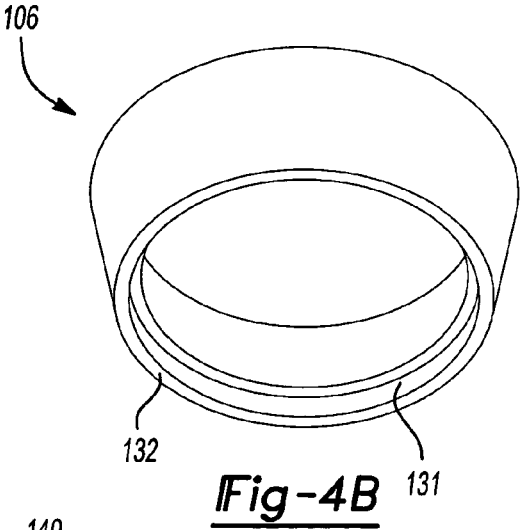

Referring to FIGS. 4A and 4B, the hollow member 106 can include an annular upper face 130, an annular lower face 132, and a peripheral wall 134 between the upper and lower faces 130, 132. The peripheral wall 134 can be tapered from the upper face 130 to the lower face 132, and can define an inner step or notch or other circumferential discontinuity 131. The hollow member 106 can be inserted around the compressible lower portion 123 such that the flanges 126 engage the discontinuity 131 and the elongated members 124 are urged radially inwards securing the hollow member 106 over the receiver 104 in a snap-fit or other engagement.

Figure 5A:
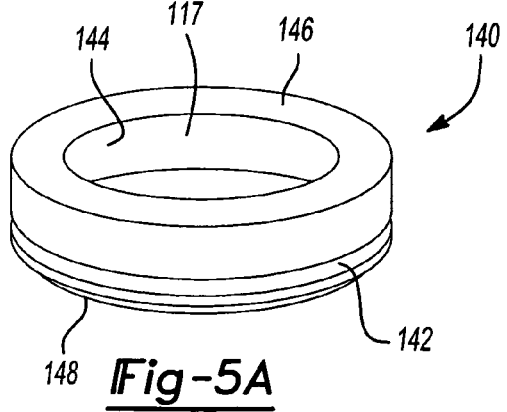
FIG. 5A is a perspective view of a cap for the multi-axial screw assembly of FIG. 1.
Figure 5B:
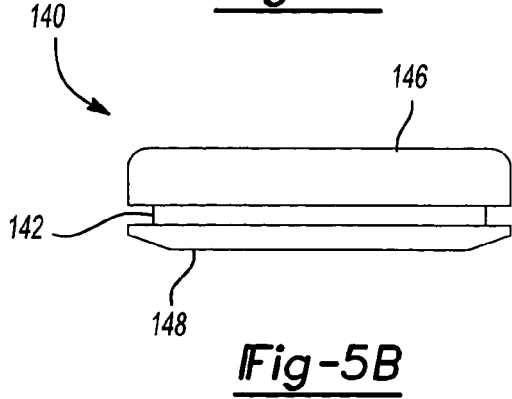
FIG. 5B is a side view of the cap of FIG. 5A.
Figure 6:
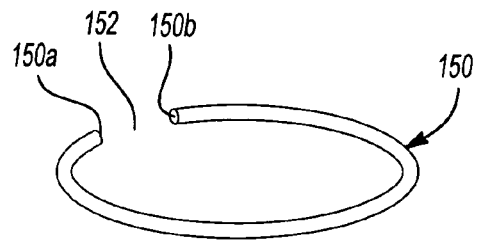
FIG. 6 is a perspective view of a cap-retaining ring for the multi-axial screw assembly of FIG. 1.
Figure 7:
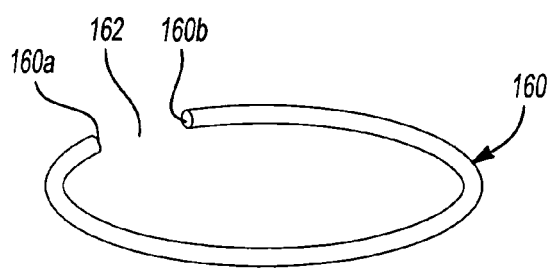
FIG. 7 is a perspective view of a bone screw ring for the multi-axial screw assembly of FIG. 1.

Referring to FIGS. 5A and 5B, the annular member 140 can include a peripheral or side wall 144 between upper and lower surfaces 146, 148. The peripheral wall 144 defines an opening 117 through the annular member 140. The annular member 140 can define a second outer circumferential groove 142 on the peripheral wall 144 for at least partially receiving the second retention element 150.

Figures 9, 10A:
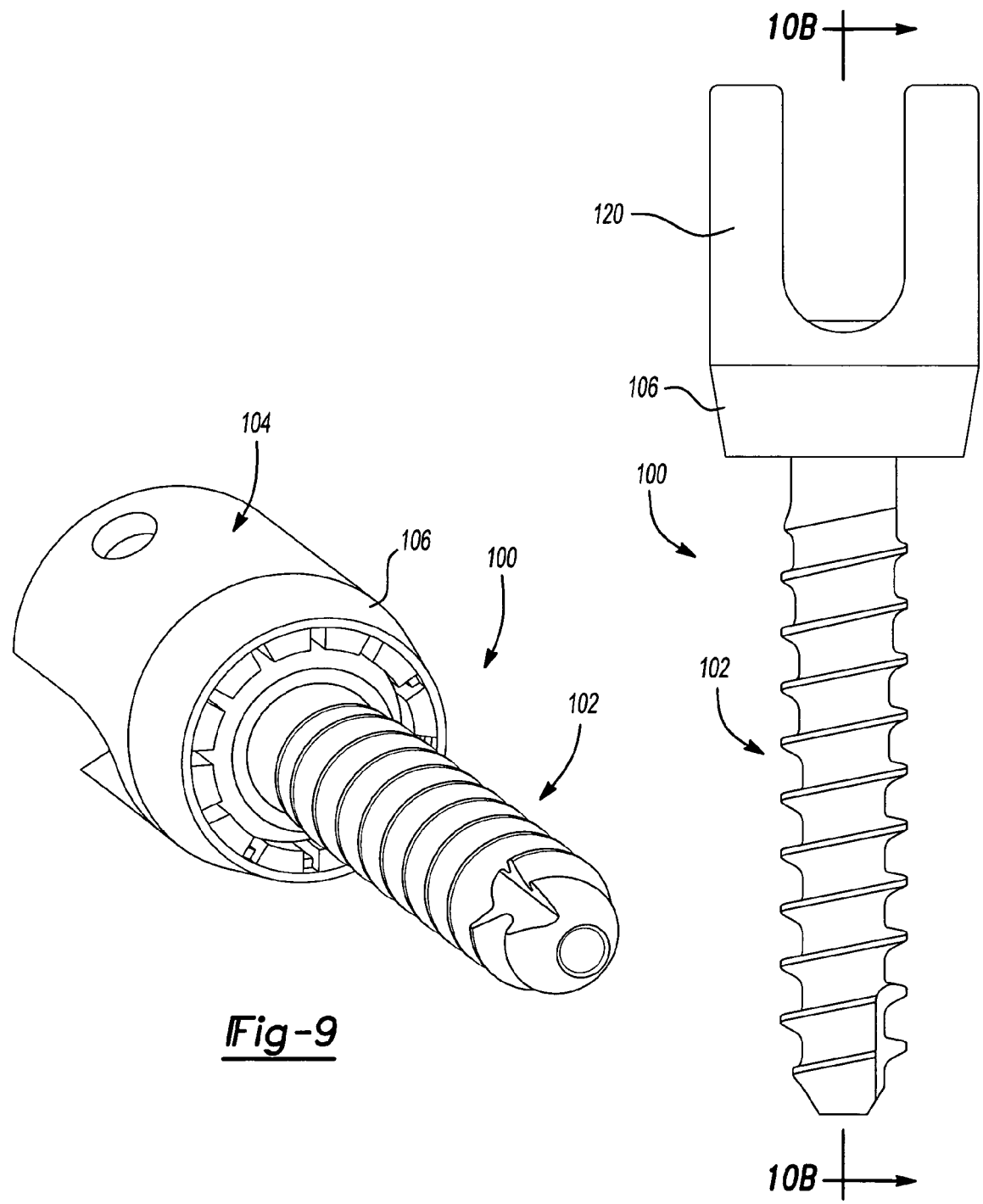
FIG. 9 is a bottom perspective view of the multi-axial screw assembly of FIG. 8D.
FIG. 10A is a side view of the multi-axial screw assembly of FIG. 9.

Referring to FIGS. 8A-8D, an exemplary procedure for assembling the multi-axial fixation device 100 can include assembling the first retention element 160 in the first circumferential groove 108 of the head 110 of the bone fastener 102, as shown in FIG. 8B, and inserting the bone fastener 102 from the lower portion 123 of the receiver 104 into the lower opening 103, as shown in FIG. 8C. As such, the elongated elements 124 in their relaxed states can cooperate to define an opening 103 larger than the diameter of the head 110. The hollow member 106 can be pushed over the lower portion 123 until the flanges 126 of the elongated elements 124 snap into the discontinuity 131 radially compressing the lower portion 123. Engagement of the hollow member 106 inwardly deflects the elongated elements 124 toward the first longitudinal axis A such that the lower opening 103 becomes smaller in diameter. The reduced diameter of the lower opening 103 is now smaller than the maximum diameter of the head 110 and thereby prevents the head 110 of the bone fastener 102 from becoming dislodged from the lower portion 123 of the receiver 104, as shown in FIGS. 8C and 9.

Figures 10B, 10C:
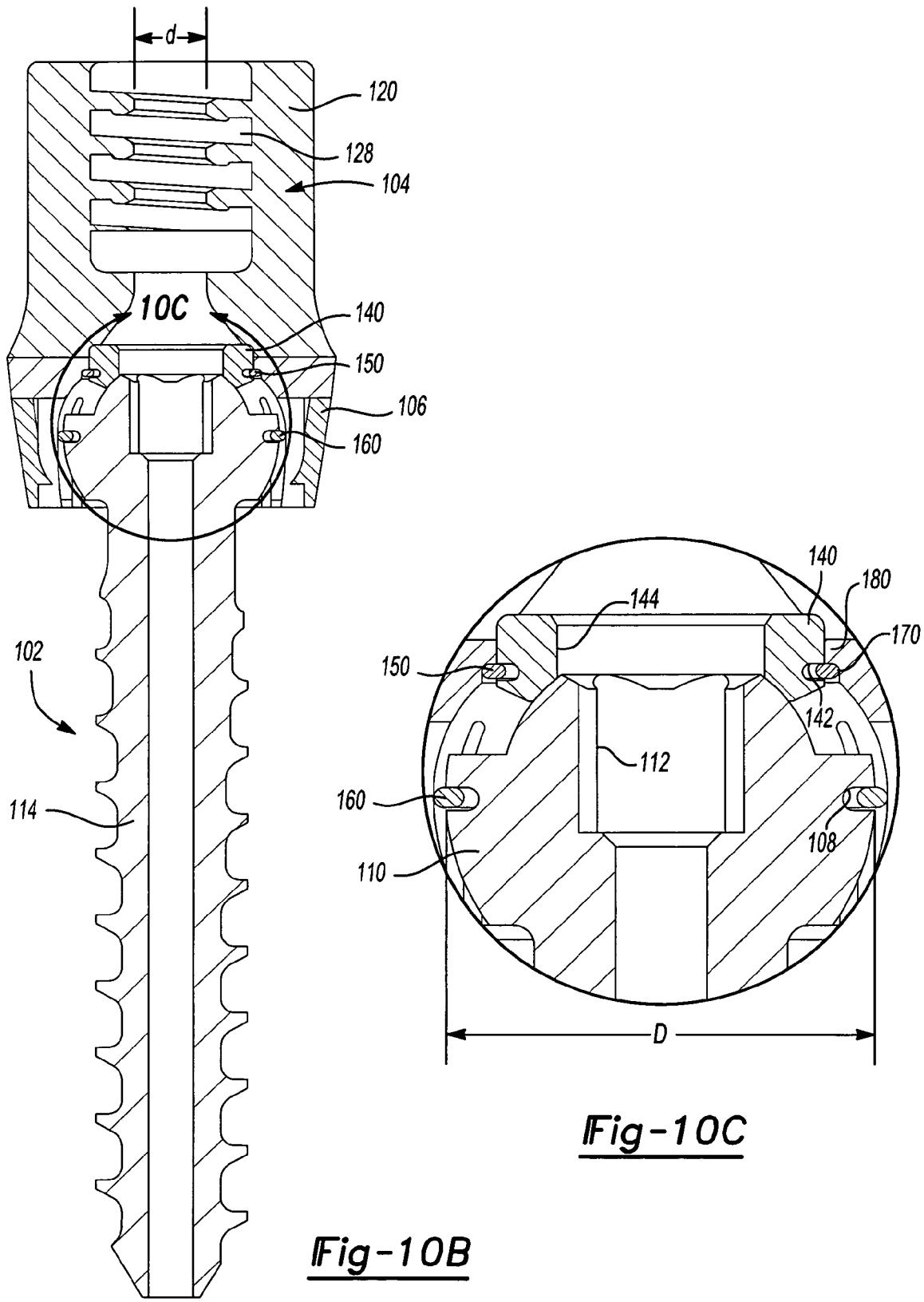
FIG. 10B is a sectional view of the multi-axial screw assembly of FIG. 9.
FIG. 10C is an enlarged view of Detail 10C of FIG. 10B.

As can be seen in FIGS. 10B and C, a major diameter D of the head 110 can exceed a minor diameter "d" of the receiver 104. The minor diameter d can correspond to the engagement formations 128. In this position, the fastener 102 can angulate relative to the first longitudinal axis A of the receiver 104, as shown in FIG. 8D in phantom lines. The first retention element 160 can provide frictional resistance to rotation of the bone fastener 102 relative to the receiver 104.

Referring to FIG. 8C, the second retention element 150 can be assembled in the second circumferential groove 142 of the annular element 140, which can be inserted from the upper portion 121 of the receiver 104 and positioned to contact the head 110 of the bone fastener 102, as shown in FIG. 8D. In one aspect the annular member 140 can be seated around the protrusion 119 of the head 110 of the bone fastener 102, such that the protrusion 119 is inserted in the opening 117 defined by the peripheral wall 144. The second retention element 150 can retain the annular member 140 in the receiver 104 and can be supported between the second circumferential groove 142 and a notch 170 defined in an abutting inner surface of the receiver 104, as shown in FIGS. 10B and 10C.

Referring to FIGS. 1 and 3A, after the annular element 140 is assembled in the receiver 104, the connecting element 109 can be inserted along the transverse axis B in the transverse opening 101 of the receiver 104. A securing or locking member 113, in the form of a set screw or other plug, for example, can be inserted through the upper opening 105 of the receiver 104. The securing member 113 can include engagement formations 111 complimentary to the engagement formations 128 of the receiver 104, and a driver-receiving inner surface 107. The engagement formations 111 can comprise a helical flange, for example. A driver can be coupled to the driver-receiving surface 107 and rotated to drive the securing member 113 against the connecting element 109, thereby transmitting compression through the annular element 140 to the head 110 of the bone fastener 102 and securing the bone fastener 102 in a pre-selected angulation position.

The multi-axial bone fixation device 100 can be used with bone fasteners 102 having different sizes or shapes, or of different types, with or without flutes 118 or other cutting ridges. For example, the extent and/or type of anchoring formations 116 can be varied, as well as the size and geometry of the head 110, etc.

It will be appreciated that the present teachings allow quick loading of the bone fastener 102 from the lower portion 123 of the receiver and still maintain a high degree of angulation similar to top-loading bone fasteners. Further, the present teachings allow a major diameter D of the head of the bone fastener 102 to exceed a minor diameter d that is associated with the engagement formations 128 for the securing element 113. Thus the present teaching can prevent bone fastener back out.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A multi-axial bone fixation device comprising:
   a receiver defining an axial opening alone a longitudinal axis, the receiver having first and second portions along the longitudinal axis, the second portion being radially compressible;
   a bone fastener having a head, the head insertable into the axial opening in a direction from the second portion to the first portion;
   a hollow member received around the second portion, the hollow member compressing the second portion and retaining the head while allowing angulation of the fastener relative to the longitudinal axis; and
   a first ring carried by the head of the fastener, the first ring maintaining a position of the fastener relative to the receiver before implantation.

2. The device of claim 1, wherein the hollow member comprises a tapered inner surface.

3. The device of claim 1, wherein the head comprises a circumferential groove, the first ring at least partially disposed in the circumferential groove.

4. The device of claim 1, further comprising an annular element insertable into the axial opening in a direction from the first portion to the second portion and positioned in contact with the head of the bone fastener.

5. The device of claim 4, wherein the annular element comprises an internal driver engagement surface.

6. The device of claim 4, further comprising a second ring carried by the annular member, the second ring securing the annular element within the axial opening of the receiver.

7. The device of claim 6, further comprising a threaded member, the threaded member threadably received into the first portion of the receiver, the threaded member holding the fastener in a fixed angle relative to the axial opening.

8. The device of claim 7, wherein the threaded member contacts an elongated element received in a transverse opening of the receiver between the threaded member and the annular member.

9. The device of claim 1, wherein the head comprises an internal driver-engagement surface.

10. The device of claim 1, wherein the second portion comprises a plurality of spaced apart elements.

11. The device of claim 10, wherein each of the spaced apart elements includes an outer flange extending proximate a distal end thereof.

12. The device of claim 10, wherein the hollow member comprises an inner circumferential discontinuity engaging the outer flanges of the spaced apart elements.

13. A multi-axial bone fixation device comprising:
   a receiver defining an axial opening along a longitudinal axis, the receiver having an upper portion and a lower portion along the longitudinal axis, the lower portion comprising a plurality of spaced apart flexible elements;
   a bone fastener having a head and a bone-engaging elongated portion, the head insertable into the axial opening along the longitudinal axis in a direction from the lower portion to the upper portion, the head having an external circumferential groove;
   a friction element supported in the circumferential groove; and
   a hollow member having a surface tapered along the longitudinal axis and received around the lower portion, the hollow member compressing the plurality of flexible elements such that the fastener is retained in the receiver and permitted to angulate relative to the longitudinal axis.

14. The device of claim 13, further comprising an annular member insertable into the axial opening from the upper portion above and in contact with the head of the fastener, the annular member having an external circumferential groove.

15. The device of claim 14, further comprising a retention element supported by the groove of the annular member.

16. The device of claim 13, wherein the hollow member defines an inner step engaging a tab extending proximate a distal end of at least one flexible element.

17. The device of claim 13, wherein the receiver has an inner threaded portion defining a minor diameter, and the head of the fastener has a major diameter larger than a minor diameter of the receiver.

18. A multi-axial bone fixation device comprising:
   a receiver defining an axial opening along a longitudinal axis, and a transverse opening along a transverse axis, the receiver having an upper portion and a lower portion along the longitudinal axis, the lower portion comprising a plurality of spaced apart elongated elements, each elongated element having a flange extending proximate a distal end thereof;
   a bone fastener having a head and a bone-engaging elongated portion, the head insertable into the axial opening along the longitudinal axis in a direction from the lower portion to the upper portion, the head having a first circumferential groove;
   an annular member insertable into the axial opening from the upper portion over the head of the fastener, the annular member having a second circumferential groove;
   a first retention element supported in the first circumferential groove;
   a second retention element supported in the second circumferential groove;
   a hollow member having a surface tapered along the longitudinal axis and received around the lower portion, the hollow member defining an inner groove engaging the flanges of the elongated elements and compressing the elongated elements such that the fastener is retained in the receiver and can angulate relative to the longitudinal axis;
   an elongated element insertable in the receiver along the transverse axis; and
   a securing element threadably received in the upper portion of the receiver over the elongated element, such that when the securing element is fully threaded to the receiver, the securing element transmits a force to the head of the fastener and secures the fastener in the receiver at a selected angle relative to the longitudinal axis.

19. The device of claim 18, wherein the head includes an inner driver engagement surface.

20. A bone fixation device comprising:
   a receiver having a deformable portion:
   a bone fastener having a head, the head insertable into the receiver from the deformable portion;
   a retaining member couplable to the deformable portion, the retaining member deforming the deformable portion and angulatably retaining the fastener relative to the receiver, the retaining member defining an opening having a tapered inner surface, the tapered inner surface compressing the deformable portion when the deformable portion is received in the opening of the retaining member; and
   a split ring at least partially disposed in a circumferential groove of the head.

21. The bone fixation device of claim 20 wherein the deformable portion comprises a plurality of spaced apart elements, each of the spaced apart elements including an outwardly extending flange.

22. The bone fixation device of claim 21, wherein the retaining member defines an inner circumferential step engaging the outer flanges of the spaced apart elements.

* * * * *